US00H002232H

(19) United States
(12) Statutory Invention Registration
Karcher et al.

(10) Reg. No.: US H2232 H
(43) Published: Sep. 1, 2009

(54) METHODS FOR TESTING FOR BIOACCUMULATION

(75) Inventors: Arron Karcher, Duncan, OK (US); O. Marlene Isenberg, Duncan, OK (US); Ian D. Robb, Duncan, OK (US); J. Michael Wilson, Duncan, OK (US)

(73) Assignee: Halliburton Energy Services, Inc., Duncan, OK (US)

(21) Appl. No.: 11/935,988

(22) Filed: Nov. 6, 2007

(51) Int. Cl.
*G01N 33/00* (2006.01)

(52) U.S. Cl. ..... 422/68.1

(58) Field of Classification Search ..... 422/68.1
See application file for complete search history.

*Primary Examiner*—Michelle Clement
(74) *Attorney, Agent, or Firm*—Baker Botts L.L.P.

(57) ABSTRACT

Methods comprising: providing a test substance, providing two solvents that are substantially immiscible, introducing a known amount of the test substance and known amounts of the two solvents into a single vessel to create a pre-equilibrium sample, adjusting the concentration of the test substance in the pre-equilibrium sample so that the concentration of the test substance is below the critical micelle concentration of both solvents if the concentration of the test substance is not already below the critical micelle concentration, allowing the test substance to equilibrate between the two solvents over time at a substantially constant temperature, determining the equilibrium concentration of the test substance in each of the solvents, and calculating the partition coefficient.

8 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHODS FOR TESTING FOR BIOACCUMULATION

BACKGROUND

The present invention generally relates to testing, measuring, analyzing or predicting bioaccumulation. More particularly, the present invention relates to methods for determining the partition coefficient of chemical substances, wherein the partition coefficient may relate to the bioaccumulation of such substances. The methods of the present invention may be particularly suitable for measuring or evaluating bioaccumulation of surfactants, although the method may also be used for measuring or evaluating bioaccumulation of other chemical substances.

Bioaccumulation is generally defined as the process through which a chemical increases in concentration in a biological organism over time when compared to the concentration of the chemical in the environment. Compounds accumulate in living things any time they are taken up and stored faster than they are broken down, metabolized or excreted. The process is normal and can be helpful to life, as in the storage of vitamins, for example. However, the process can result in injury to life when the equilibrium between exposure and bioaccumulation is overwhelmed. The extent of bioaccumulation depends on the concentration of the chemical in the environment, the amount of chemical coming into an organism from the food, air or water, and the time it takes for the organism to acquire the chemical and then store, metabolize or degrade, and excrete it. The nature of the chemical itself, such as its solubility in water and fat, affects its uptake and storage; the ability of the organism to degrade and excrete the chemical also affects its uptake and storage. Understanding the dynamic process of bioaccumulation is generally viewed as important in protecting humans and other organisms from adverse effects from chemical exposure. Consequently, bioaccumulation has become a critical consideration in the regulation of chemicals.

Industries using chemicals in the environment are increasingly faced with regulations concerning bioaccumulation of those chemicals. The oil and gas industry has varying guidelines and regulations in many countries worldwide relating to chemicals used in the search for and production of hydrocarbons from subterranean formations in those countries. Some regulations require testing of individual components of chemicals used. For compliance with such guidelines and regulations, the industry tests its chemicals and chemical components, often by test methods or techniques also prescribed, recommended, and/or approved in the guidelines or regulations.

Guidelines and regulations pertaining to bioaccumulation frequently refer to a value known as a substance's partition coefficient. The partition coefficient, often represented as "P" or written in the form of its logarithm to base ten, "log P," is the ratio of the equilibrium concentrations of a dissolved substance in a two-phase system consisting of two largely immiscible solvents. For example, the partition coefficient of a test substance in solvents n-octanol and water may be written as $P_{ow}$, and calculated as the quotient of the equilibrium concentration of the test substance in n-octanol ($C_{n\text{-}octanol}$) and the equilibrium concentration of the test substance in water ($C_{water}$), expressed as follows:

$$P_{ow} = \frac{C_{n\text{-}octanol}}{C_{water}}$$

The partition coefficient for octanol and water solvents, $P_{ow}$, is a key parameter in studies of the environmental impact of chemical substances. The Organisation for Economic Co-operation and Development's ("OECD") Guideline for Testing of Chemicals No. 117 states that there is a highly significant relationship between the $P_{ow}$ of substances and their bioaccumulation in fish and that $P_{ow}$ is useful in predicting adsorption on soil and sediments and in establishing quantitative structure-activity relationships for a wide range of biological effects.

One test that has been used to determine the partition coefficient for n-octanol and water is the High Performance Liquid Chromatography (HPLC) Method described in the OECD Guideline for Testing of Chemicals No. 117, incorporated herein in its entirety by reference and available from OECD in Paris, France. This test is performed on analytical columns packed with a commercially available solid phase containing long hydrocarbon chains (e.g., $C_8$–$C_{18}$) chemically bound onto silica. Chemicals injected onto such a column move along it by partitioning between the mobile solvent phase and the hydrocarbon stationary phase. The chemicals are retained in proportion to their hydrocarbon-water partition coefficient, with water-soluble chemicals eluted first and oil-soluble chemicals eluted last. This pattern enables the relationship between the retention time on a reverse-phase column and the n-octanol/water partition coefficient to be established. The partition coefficient is deduced from the capacity factor, k, given by the formula:

$$k = \frac{t_R - t_o}{t_o}$$

where $t_R$ is the retention time of the test substance, and $t_o$ is the dead-time, i.e., the average time an unretained molecule needs to pass through the column. Quantitative analytical methods are not needed and only the retention times are measured.

In general, before the $P_{ow}$ value is determined through a test such as the HPLC Method, a preliminary estimate of $P_{ow}$ is made using known calculations. This preliminary estimate may then be used to select which test will be used to measure the $P_{ow}$ value more precisely, as certain tests may only be able to reliably determine $P_{ow}$ values within a limited range. For example, the HPLC Method is useful in determining $P_{ow}$ values when log $P_{ow}$ is in the range between 0 and 7. When the log $P_{ow}$ value is estimated to be in the range between −2 and 4, another test has been used. That test is the OECD Guideline for Testing of Chemicals No. 107, called the Partition Coefficient (n-octanol/water): Shake-Flask Method, which is incorporated herein in its entirety by reference and available from the OECD in Paris, France.

The Shake-Flask Method is based on the principle that the Nernst partition law applies at constant temperature, pressure and pH for dilute solutions. OECD Guideline No. 107 states that the law strictly applies to a pure substance dispersed between two pure solvents and when the concentration of the solute in either phase is not more than 0.01 mole per liter. If several different solutes occur in one or both phases at the same time, the results may be affected. Dissociation or association of the dissolved molecules cause deviations from the partition law.

Neither the HPLC Method nor the Shake-Flask Method is suitable for calculating the partition coefficients for chemicals that are considered surface active, or surfactants. Nevertheless, surfactants are commonly used in drilling and well treating fluids. It has been previously disclosed that a slow-stirring or no-stirring method may be used to determine the partition coefficients of various surfactants. According to those methods, once a quantity of surfactant has been allowed to equilibrate between two immiscible solvents, the equilibrium concentration of the surfactant in each solvent may be measured and the partition coefficient may be calculated. One problem that may arise during the performance of these methods is the formation of surfactant micelles. It is well understood that when molecules (or ions) of a test substance such as a surfactant are mixed with a solvent in a concentration above the critical micelle concentration ("CMC"), the molecules (or ions) may associate to form micelles. The term "micelle" is defined to include any structure that minimizes the contact between the lyophobic ("solvent-repelling") portion of a test substance molecule and the solvent, for example, by aggregating the test substance molecules into structures such as spheres, cylinders, or sheets, wherein the lyophobic portions are on the interior of the aggregate structure and the lyophilic ("solvent-attracting") portions are on the exterior of the structure. Because the presence of micelles in a solvent may distort the readings of the equilibrium concentration of the test substance in the solvent, prior art methods that do not take steps to ensure that micelles will not form during equilibration may not yield accurate measurements of the equilibrium concentration. Micelles may also be problematic because, inter alia, micelles may be related to the problematic emulsification of the substances being tested.

The present invention generally relates to testing, measuring, analyzing or predicting bioaccumulation. More particularly, the present invention relates to methods for determining the partition coefficient of chemical substances, wherein the partion coefficient may relate to the bioaccumulation of such substances. The methods of the present invention may be particularly suitable for measuring or evaluating bioaccumulation of surfactants, although the method may also be used for measuring or evaluating bioaccumulation of other chemical substances.

In some embodiments, the present invention provides a method comprising: providing a test substance, providing two solvents that are substantially immiscible, introducing a known amount of the test substance and known amounts of the two solvents into a single vessel to create a pre-equilibrium sample, adjusting the concentration of the test substance in the pre-equilibrium sample so that the concentration of the test substance is below the critical micelle concentration of both solvents if the concentration of the test substance is not already below the critical micelle concentration, allowing the test substance to equilibrate between the two solvents over time at a substantially constant temperature, determining the equilibrium concentration of the test substance in each of the solvents, and calculating the partition coefficient.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

DESCRIPTION OF PREFERRED EMBODIMENTS

Figure 1:
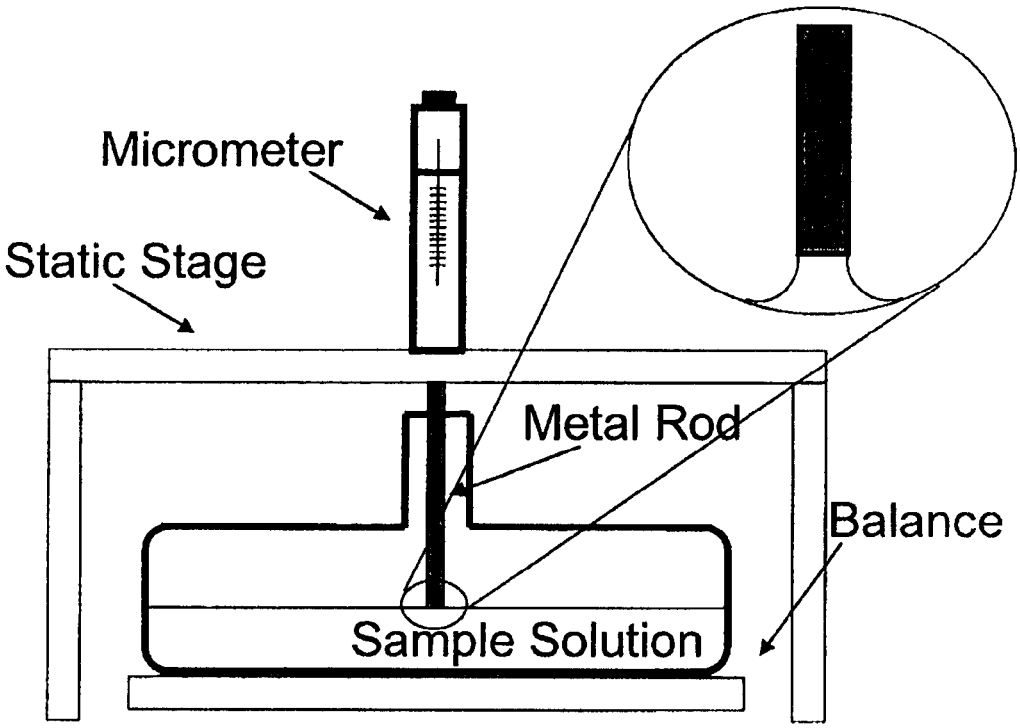
FIG. 1 is a schematic illustration of a device that may be used to determine the surface tension of a sample solution.

The present invention generally relates to testing, measuring, analyzing or predicting bioaccumulation. More particularly, the present invention relates to methods for determining the partition coefficient of chemical substances, wherein the partition coefficient may relate to the bioaccumulation of such substances. The methods of the present invention may be particularly suitable for measuring or evaluating bioaccumulation of surfactants, although the method may also be used for measuring or evaluating bioaccumulation of other chemical substances.

In some embodiments, the present invention provides methods comprising providing a test substance; providing two solvents that are substantially immiscible; introducing a known amount of the test substance and known amounts of the two solvents into a single vessel to create a pre-equilibrium sample; adjusting the concentration of the test substance in the pre-equilibrium sample so that the concentration of the test substance is below the critical micelle concentration of both solvents, if the concentration of the test substance is not already below the critical micelle concentration; allowing the test substance to equilibrate between the two solvents over time at a substantially constant temperature; determining the equilibrium concentration of the test substance in each of the solvents; and calculating the partition coefficient.

There may be several potential advantages to the methods of the present invention. One such advantage may be these methods calculate partition coefficients based on experimental conditions that approximate environmental conditions more closely than some prior art methods. In environments in which bioaccumulation is a concern, the concentration of a surfactant is usually low, e.g., below the critical micelle concentration ("CMC") of the surfactant in environmental solvents. Therefore, a method of calculating the partition coefficient of a surfactant based on a pre-equilibrium concentration of the surfactant that is below the CMC might better simulate bioaccumulation conditions than methods in which the initial surfactant concentration exceeds the CMC. Another advantage of the methods of the present invention may be that by ensuring that the initial concentration of a test substance in two immiscible solvents is below the CMC of either solvent, it may be expected that once the test substance is allowed to equilibrate between the solvents, no micelles will be present in either solvent. This absence of micelles may be desirable, because in some cases micelles may interfere with the measurement of the equilibrium concentrations.

In some embodiments of the present invention, the two solvents that are substantially immiscible may be any two substantially immiscible solvents that do not adversely interact with each other, with the test substance, or with any other substance used in the testing methods. Suitable pairs of solvents may include, but are not limited to, certain oils with certain alcohols, and water with certain alcohols. In some embodiments in which one of the solvents is water, the water may be distilled or double-distilled. In other embodiments in which one of the solvents is water, the water may comprise buffered water, salt water, sea water, synthetic sea water, or the like. In some preferred embodiments, the solvents may be water and octanol. In embodiments in which octanol is one of the solvents, the octanol is preferably of analytical grade or higher.

In some embodiments, one or both of the two substantially immiscible solvents may be pre-saturated with some quantity of the other solvent. In preferred embodiments, the solvent that is being pre-saturated may be pre-saturated with about 10% of the other solvent for at least 24 hours. That is, for example, a water solvent may be pre-saturated with about 10% octanol and/or an octanol solvent may be pre-saturated with about 10% water. By way of explanation and not of limitation, pre-saturating a solvent with the other solvent may be advantageous, because no two solvents are completely immiscible. Pre-saturation may allow a solvent to reach equilibrium prior to the equilibration of the test substance.

In general, the test substance for which the partition coefficient is calculated may be any substance that may be tested for a tendency to accumulate in a biological organism. In some preferred embodiments, the test substance may comprise a surface active chemical or surfactant. As previously indicated, in preferred embodiments the step of adjusting the concentration of the test substance in the pre-equilibrium sample to a concentration below the CMC of the test substance in both solvents may prevent the formation of micelles when the test substance is allowed to equilibrate between the two solvents.

In some embodiments, the step of adjusting the concentration of the test substance in the pre-equilibrium sample to a concentration below the CMC of the test substance in both solvents may be performed without quantifying or otherwise determining the CMC's. For example, individual solutions that comprise the test substance and one of the solvents in the same relative amounts as those substances are present in the pre-equilibrium sample may be prepared. Then, a dynamic light scattering technique may be used to detect the presence of micelles in each individual solution. Dynamic light scattering techniques are well known, and a person of skill in the art would understand how dynamic light scattering may be used to detect the presence of micelles. In general, dynamic light scattering involves shining a light through a solution. The presence of micelles in the solution is detected when a point source center, e.g., a micelle of sufficient size, back-scatters the light. The amount and pattern of back-scattering may correspond to the number and/or size of micelles present in the solution. In order to ensure that the concentration of the test substance in a solvent is below the critical micelle concentration, the individual solutions may be serially diluted with more of the same solvent until no micelles are detected. The pre-equilibrium sample may then be diluted to the same or lower dilution.

In some embodiments, the methods of the present invention may comprise the step of determining the CMC of the test substance in one or both of the solvents, e.g., predicting, quantifying, and/or extrapolating the CMC. In preferred embodiments, the step of determining the CMC of the test substance in either solvent is carried out before the step of adjusting the concentration of the test substance in the pre-equilibrium sample to a concentration below the CMC of the test substance in the solvents. In general, the critical micelle concentration of a test substance in a solvent may be determined through any method known in the art for determining critical micelle concentration. Suitable methods for determining critical micelle concentration include, for example, the use of an inverted vertical pull surface tension method (e.g., a rod-pull tensiometer), and particle size analysis (e.g., photon correlation measurements, dynamic light scattering methods, and the like). In embodiments in which it may be difficult to measure the critical micelle concentration through surface tension methods, it may be preferable to use particle size analysis techniques, and vice versa. In some embodiments of the present invention in which a solvent comprises a long chain alcohol and the test substance comprises a surfactant, it may be especially important to experimentally determine the CMC of the test substance in the solvent. By way of explanation and not of limitation, this preference arises from the tendency of long chain alcohols to substantially lower the CMC of some surfactants, especially ionic molecules.

In some embodiments in which dynamic light scattering is used to determine the CMC of a test substance in a solvent, dynamic light scattering tests are repeated at various concentrations of the test substance in the solvent. Then the number of micelles present at the various concentrations may be plotted as a function of text substance concentration, and the CMC may be extrapolated as the higher concentration of test substance at which no micelles are detected. Dynamic light scattering may be particularly well suited for determining the CMC of a test substance in a solvent when the solvent is highly purified water. In certain embodiments in which a water solvent has been presaturated with octanol, other methods for determining the CMC may be preferred over dynamic light scattering. By way of explanation and not of limitation, dynamic light scattering may not be the preferred method of determining the CMC of octanol-saturated water, because the octanol may distort micelle shape, which can affect the number of micelles detected. In some embodiments in which an alcohol other than octanol may be used, that alcohol might also be responsible for distorting micelle shape.

In some embodiments of the present invention, inverted vertical pull surface tension methods may be used to determine the CMC of a test substance in a solvent. In some embodiments, inverted vertical pull surface tension methods may comprise placing a solution of a test substance in a single solvent on a balance; lowering a rod until it touches the surface of the solution; taring the balance; and then slowly raising the rod from the solution. The maximum weight reduction that registers on the balance as the rod is lifted can be used to calculate the surface tension of the solution. Methods of calculating the surface tension from the maximum weight reduction are well known in the art. For example, the calculations outlined in Christian et al., LANGMUIR 1998, 14, 3126-28 and Christian et al., J. COLLOID AND INTERFACE SCI., 1999, 214, 224-30 may be used. In general, these calculations may also take into account factors other than the test substance concentration, such as temperature, density, etc. By repeating the inverted pull surface tension test at multiple concentrations of the test substance in the solvent and plotting the calculated surface tensions as a function of test substance concentration, the CMC may be extrapolated. In general, the CMC is extrapolated as the lowest concentration of test substance at which the surface tension would have become constant despite further increases in concentration. One example of a device that may be used to carry out an inverted pull surface tension method is the rod-pull tensiometer available from Temco, Inc. of Tulsa, Okla. under the trade name EZ TENSIOM- ETER. FIG. 1 shows a schematic representation of one type of device that may be suitable for inverted vertical pull surface tension methods.

In some embodiments, after the two solvents and the test substance are introduced into a vessel to create a pre-equilibrium sample, the test substance is allowed to equilibrate between the two solvents during a slow-stir (or no-sti)r procedure typically conducted in a laboratory or under laboratory type conditions using laboratory type equipment. In preferred embodiments, allowing the test substance to equilibrate between the two solvents may comprise stirring the pre-equilibrium sample over time. It is believed that in certain embodiments stirring may reduce the time necessary for equilibration.

In preferred embodiments, the pre-equilibrium sample is stirred at a constant temperature (e.g., varying by less than 1° C.) and at a slow rate so that emulsions do not begin to form. The temperature selected may be any temperature that is below the boiling point of the two solvents and the test substance. For an octanol-water solvent system, a temperature selected from the range of about 20° C. to about 22° C. is preferred, although higher temperatures such as about 25° C. may alternatively be used. Generally, the stirring speed (if any) selected will depend on the size and shape of the container and the length of the stirring bar (if a stirring bar is used), as well as the ease with which the solvents form emulsions. For surfactants generally, a stir rate that creates a vortex no greater than simply reaching from the top to the bottom of the vessel may often be preferred, or more preferably a stirring rate that creates a vortex that does not exceed about one-fifth the height of the total fluid column. In some preferred embodiments, the ratio of length of the fluid column-to-height of the vortex may be in the range of about 1 (for the case where the vortex extends from the top to the bottom of the container) to infinity ∞ (for the case of no stirring). In one exemplary embodiment wherein the vessel containing the pre-equilibrium sample has dimensions of about 27.5 mm×70 mm, a vortex of about 15 mm or less may be preferred. This arrangement would provide a ratio of length of the fluid column-to-height of the vortex of about 4.667. To achieve such a ratio in this example configuration, a stirring rate of about 150 rpm may be used. However, speeds ranging from about 0 rpm to about 200 rpm, for example, may be appropriate for use with most surfactants in a similarly sized vessel.

After allowing the test substance to begin to equilibrate between the two solvents, with or without such stirring, typically for several days or weeks, and preferably after equilibrium is reached, the concentration of the test substance in each immiscible layer is measured. For example, the concentration of the test substance in a water layer ($C_{water}$) and the concentration of the test substance in an octanol layer ($C_{n\text{-}octanol}$) are measured. From these, a partition coefficient, for example $P_{ow}$, for the test substance is calculated using the following formula:

$$P_{ow} = \frac{C_{n\text{-}octanol}}{C_{water}}$$

If solvents other than water and n-octanol are used, the heavier solvent is substituted for the $C_{water}$ in the formula and the lighter solvent is substituted for the $C_{n\text{-}octanol}$ in the formula, as follows:

$$P = \frac{C_{(lighter\ solvent)}}{C_{(heavier\ solvent)}}$$

Samples for this concentration analysis are taken from each solvent layer, for example the water layer and the octanol layer, preferably immediately after stirring but in any case before about 1 hour has lapsed after stirring has ceased or after equilibrium is believed to have been reached. These samples may then be immediately analyzed for content and concentration of the test substance or may be stored, preferably at a constant temperature in the range of about 20° C. to about 22° C. or at room temperature, for later analysis. Measurement of the concentration of the test substance may be conducted with any equipment capable or suitable for this purpose. For example, a light scattering detector or an ionized mass detector (mass spectroscopy) is preferred when the test substance is a surfactant as these instruments are capable of measuring concentrations of surfactants below their critical micelle concentration (CMC). When the test substance has no chromaphore for detection, an evaporative light scattering detector is preferred.

Preferably, such sampling and measurements of the test substance concentration in each layer and calculation of the partition coefficient and log $P_{ow}$ value ( or log P value if solvents other than octanol and water are used) are made periodically during the test to better ascertain when equilibrium is reached. Equilibrium is considered reached when the log P value does not vary more than about 0.3 per measurement, or when the test substance concentration in the layers appears stable. At equilibrium, the P value and the log P value are final values for the test substance and are available for use in evaluating bioaccumulation of the test substance.

EXAMPLES

Example 1

Figure 2A:
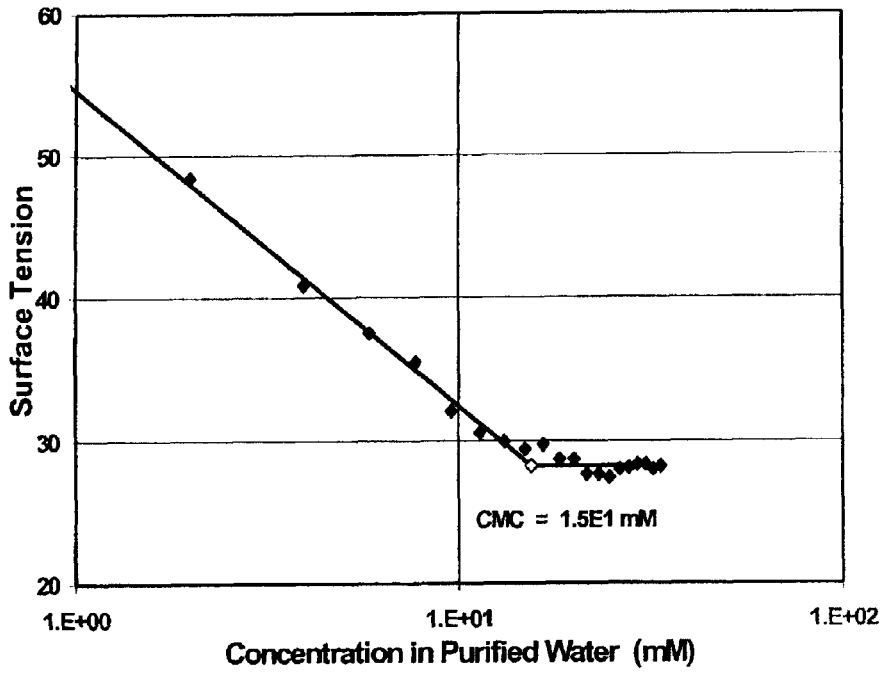
FIG. 2A is a graphical representation of the surface tension of a example surfactant A in purified water as a function of surfactant concentration. The hollow diamonds represent the extrapolated critical micelle concentration.
Figure 2B:
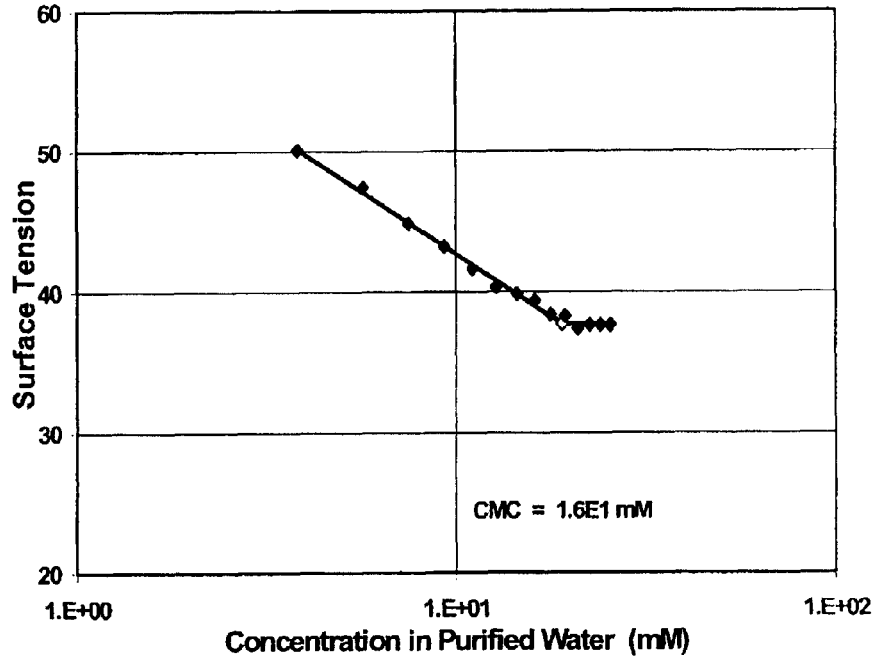
FIG. 2B is a graphical representation of the surface tension of an example surfactant B in purified water as a function of surfactant concentration. The hollow diamonds represent the extrapolated critical micelle concentration.

In order to demonstrate how the CMC of a surfactant in highly purified water might be determined through vertical pull surface tension methods, the following experiment was performed. First, two test surfactants, surfactants A and B were selected. Two sample solutions were made by combining a known quantity of purified water with a known amount of surfactant A or B, respectively. The sample solution was placed on the balance plate of an EZ TENSIOMETER obtained from Temco, Inc. of Tulsa, Okla. A schematic illustration of an example tensiometer configured to measure the surface tension of a sample solution is shown in FIG. 1. In the test, the metal rod of the tensiometer was lowered until it touched the solution and then slowly raised from the solution. Using the reduction in the solution's weight as the rod pulled some of the solution from the balance, the surface tension of the solution was calculated. The experiment was repeated with sample solutions comprising different concentrations of surfactants A and B. The calculated surface tensions were plotted as a function of concentration, as shown in FIG. 2. The extrapolation of the CMCs of surfactants A and B can also be seen in FIG. 2.

Example 2

Figure 3A:
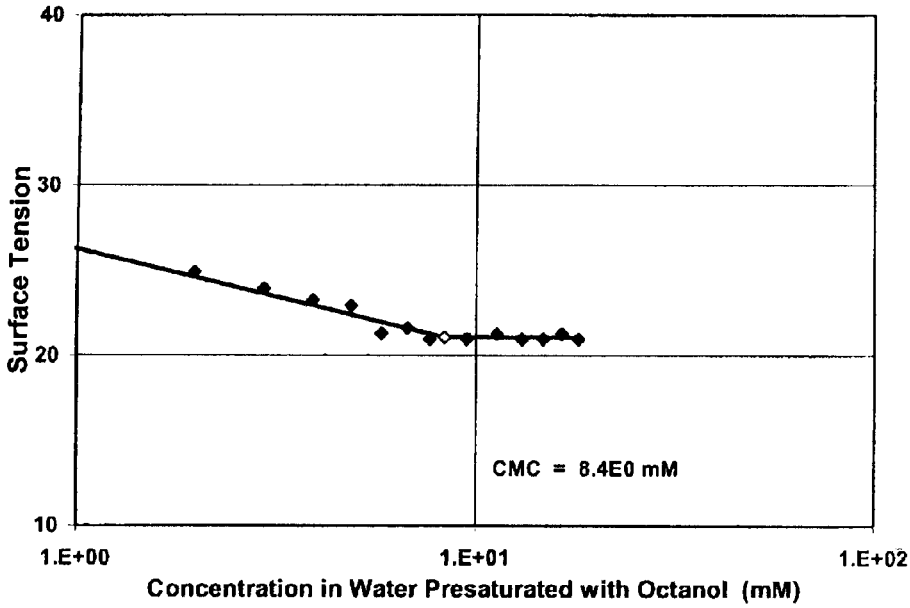
FIG. 3A is a graphical representation of the surface tension of an example surfactant A in purified water presaturated with octanol as a function of surfactant concentration. The hollow diamonds represent the extrapolated critical micelle concentration.
Figure 3B:
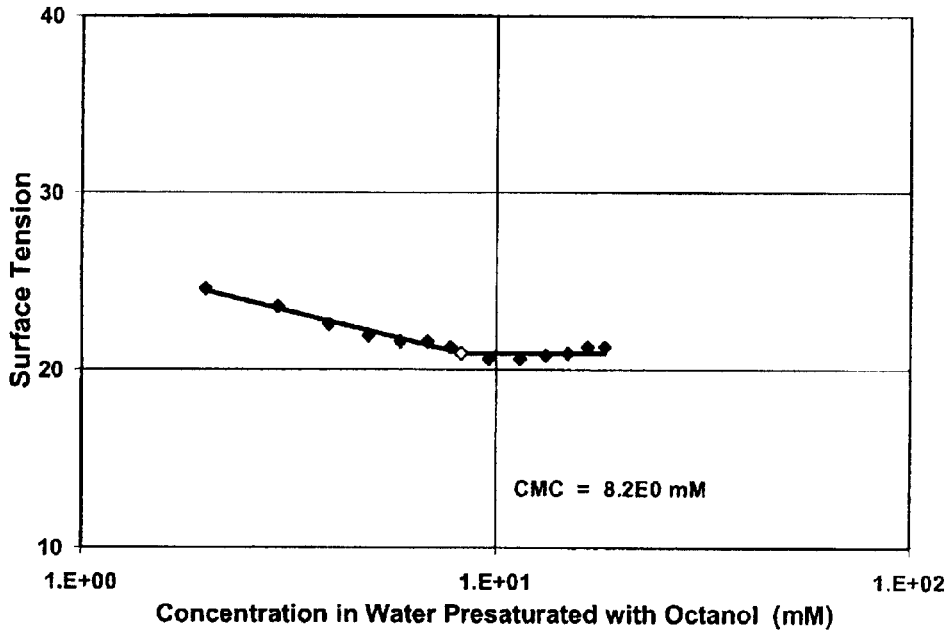
FIG. 3B is a graphical representation of the surface tension of an example surfactant B in purified water presaturated with octanol as a function of surfactant concentration. The hollow diamonds represent the extrapolated critical micelle concentration.

To investigate the effect of a long chain alcohol on the CMC of surfactants A and B, the procedures described in Example 1 were repeated using a solvent of purified water that had previously been saturated with octanol for 24 hours. The results of these tests are shown in FIG. 3, from which it is apparent that the CMC of surfactant A in the octanol-saturated water was 44% lower than in pure water, and the CMC of surfactant B in the octanol-saturated water was 49% lower than in pure water.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In particular, every range of values (of the form, "from about a to about b," or, equivalently, "from approximately a to b," or equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee.

What is claimed is:

1. A method comprising:

providing a test substance;

providing two solvents that are substantially immiscible;

introducing a known amount of the test substance and known amounts of the two solvents into a single vessel to create a pre-equilibrium sample;

adjusting the concentration of the test substance in the pre-equilibrium sample so that the concentration of the test substance is below the critical micelle concentration of both solvents, if the concentration of the test substance is not already below the critical micelle concentration;

allowing the test substance to equilibrate between the two solvents over time at a substantially constant temperature;

determining the equilibrium concentration of the test substance in each of the solvents; and calculating the partition coefficient.

2. The method of claim 1 wherein the step of allowing the test substance to equilibrate between two solvents over time at constant temperature comprises stirring the pre-equilibrium sample at a rate that sufficiently slow to avoid the creation of an emulsion.

3. The method of claim 1 wherein the test substance is a surfactant.

4. The method of claim 1 wherein the solvents are water and n-octanol.

5. The method of claim 4 wherein the constant temperature is in the range of from about 20° C. to about 22° C.

6. The method of claim 1 wherein the constant temperature is below the boiling point of the solvents and the test substance.

7. The method of claim 1 wherein the time required for the test substance to equilibrate between the two solvents extends over several days or weeks.

8. The method of claim 4 wherein the step of calculating the partition coefficient comprises performing the following calculation:

$$P_{ow} = \frac{C_{n\text{-}octanol}}{C_{water}}$$

wherein $C_{n\text{-}octanol}$ is the equilibrium concentration of test substance in the octanol solvent, and $C_{water}$ is the equilibrium concentration of the test substance in the water solvent.

* * * * *